United States Patent [19]
Yocum et al.

[11] Patent Number: 5,422,267
[45] Date of Patent: Jun. 6, 1995

[54] INDUSTRIAL YEAST COMPRISING AN INTEGRATED GLUCOAMYLASE GENE

[75] Inventors: Robert R. Yocum, 180 Jason St., Arlington, Mass. 02174; Robert S. Daves, Reading; Michael C. Chen, Lexington, both of Mass.

[73] Assignee: Robert R. Yocum, Lexington, Mass.

[21] Appl. No.: 471,673

[22] Filed: Jan. 24, 1990

Related U.S. Application Data

[63] Continuation of Ser. No. 864,785, May 19, 1986, abandoned, which is a continuation-in-part of Ser. No. 736,450, May 21, 1985, abandoned, and a continuation-in-part of Ser. No. 736,565, May 21, 1985, abandoned, which is a continuation-in-part of Ser. No. 612,796, May 22, 1984, abandoned.

[51] Int. Cl.⁶ ......................... C12N 1/19; C12N 9/34
[52] U.S. Cl. ............................. 435/254.21; 435/205
[58] Field of Search ............... 435/205, 172.3, 317.1, 435/940, 942, 255, 254.21, 255.2; 935/28, 56, 69

[56] References Cited

U.S. PATENT DOCUMENTS

| | | | |
|---|---|---|---|
| 4,477,571 | 10/1984 | Chang | 435/252.33 |
| 4,727,028 | 2/1988 | Santerre et al. | 435/240.2 |
| 4,859,596 | 8/1989 | Hollenberg et al. | 435/172.3 |

FOREIGN PATENT DOCUMENTS

| | | |
|---|---|---|
| 0103409 | 3/1984 | European Pat. Off. . |
| 0120551 | 10/1984 | European Pat. Off. ...... C12N 15/00 |
| 0126206 | 11/1984 | European Pat. Off. . |
| 0128743 | 12/1984 | European Pat. Off. . |
| 0139114 | 5/1985 | European Pat. Off. . |
| 0163491 | 12/1985 | European Pat. Off. . |
| 8402921 | 8/1984 | WIPO ......................... C12N 15/00 |
| 8404539 | 11/1984 | WIPO . |
| 8603778 | 7/1986 | WIPO . |

OTHER PUBLICATIONS

Jimenez et al. (1980), Nature 287: 869–871.
Webster et al. (1982), "Direct Selection for G418–Resistant *Saccharomyces cerevisiae* Following Transformation with a Vector Carrying the G418–Resistance Element Tn 903", Abstracts, 11th International Conference on Yeast Genetics and Molecular Biology, p. 116.
Naumovski et al. (1983), Gene, vol. 22, pp. 203–209.
Jensen, R. et al Proc Natl Acad Sci 80 pp. 3035–3039 (1983).
Orr–Weaver, T. L. et al Methods in Enzymology 101 (C) pp. 228–245 (1983).
Tollervey, D. et al Cell 35 (2) pp. 753–762 (1983).
Gritz, W. et al Gene 25 (1983) pp. 179–188.
Scherer, S. et al Proc Natl Acad Sci 76 (10) pp. 4951–4955 (1979).
Guarente, L. et al Proc Natl Acad Sci 78(4) pp. 2199–2203 (1981).
Struhl, K. Gene 26 pp. 231–242 (1983).
Orr–Weaver et al. Proc. Natl. Acad. Sci. USA vol. 78 No. 10 pp. 6354–6358 Oct. 1981 Genetics "Yeast transformation".
Yamashita et al. Fac. Engl, Hiroshima Univ., Higashi-Hiroshima, Japan 724). Agric. Biol. Chem. 1983, 47(11) 2689–92 (Eng.).
Boel et al. The Embo Journal vol. 3 No. 5 pp. 1097–1102, 1984 "Glucoamylases . . . ".
Innis et al. (1985) Science 228:21–26.
Erratt (1980) Ph.D. Thesis–University of Western Ontario pp. 17–19.
Nunberg et al. (1984) Mol. and Cell Bio. 4(11):2306–2315.
Svensson et al. (1983) Carlsberg Res. Comm. 48:529–544.

(List continued on next page.)

*Primary Examiner*—Richard A. Schwartz
*Assistant Examiner*—Philip W. Carter
*Attorney, Agent, or Firm*—Fish & Richardson

[57] ABSTRACT

A vector having a gene for resistance to an antibiotic otherwise capable of killing a host yeast cell, the gene being transcribed from a yeast promoter sequence and the vector being capable of being integrated into a chromosome of the host yeast cell; and a diploid or greater ploidy yeast cell transformed by such a vector with heterologous DNA.

56 Claims, 7 Drawing Sheets

OTHER PUBLICATIONS

Yamashita et al., *Agric. Biol. Chem.*, "Secretion of *Saccharomyces diastaticus*", 48:1931–1932 (1984).

Meaden et al., *J. of The Institute of Brewing*, (Summaries of Posters), "A plasmid vector system for the genetic manipulation of brewing strains", (Jun. 2–7, 1985).

Struhl, *Nature*, "The new yeast genetics", 305:391–397 (Sep. 1983).

Panchal et al., *Food Technology*, "Genetic manipulation of brewing and related yeast strains", 156:99–111 (Feb. 1984).

Meaden et al., *Gene*, "A DEX gene conferring production of extracellular amyloglucosidase on yeast", 34:325–334 (1985).

Dickson, *Gene*, "Expression of a foreign eukaryotic gene in *Saccharomyces cerevisiae*: β-galactosidase from *Kluyveromyces lactis*", 10:347–356 (1980).

Webster et al., *Gene*, "Direct selection of *Saccharomyces cerevisiae* resistant to the antibiotic G418 following transformation with a DNA vector carrying the kanamycin–resistance gene of $Tn^{903}$", 26:243–252 (1983).

Miller et al., *Nature*, "Identification and comparison of two sequence elements that confer cell-type specific transcription in yeast", 314:598–603 (Apr. 1985).

Tubb, *Brewer's Guardian*, "Genetic development of yeast strains", pp. 34–37 (Sep. 1984).

Panchal et al., *Applied and Environmental Microbiology*, "Susceptiblility of *Saccharomyces* spp. and *Schwanniomyces* spp. to the aminoglycoside antibiotic G418", 47:1164–1166 (May 1984).

Penttilä et al., *Mol Gen Genet*, "Cloning of *Aspergillus niger* genes in yeast. Expression of the gene coding Aspergillus β-glucosidase", 194:494–499 (1984).

Ruby et al., *Methods in enzymology*, "Cloning regulated yeast genes from a pool of *lacZ* fusions", 101:253–269 (1983).

5' -AATTCTACTCGCCCTGAGCGGCCTCGTCTGCACAGGGTTGGCAAATGTGATTTCCAAG
    GATGAGCGGGACTCGCCGGAGCAGACGTGTCCCAACCGTTTACACTAAAGGTTCGCGC- 5'

INDUSTRIAL YEAST COMPRISING AN INTEGRATED GLUCOAMYLASE GENE

This is a continuation of application Ser. No. 6/864,785 filed on May 19, 1986, now abandoned, which is a continuation-in-part of U.S. Ser. No. 736,450, filed May 21, 1985, abandoned, and this application is also a continuation-in-part of U.S. Ser. No. 736,565, filed May 21, 1985, now abandoned, which in turn is a continuation-in-part of U.S. Ser. No. 612,796, filed May 22, 1984, abandoned.

BACKGROUND OF THE INVENTION

Technology currently exists for introducing heterologous (i.e., modified or foreign) genes into laboratory strains of yeast of the genus Saccharomyces, particularly S. cerevisiae. Two types of plasmid vectors have been used for this purpose, replicating and integrating. Replicating vectors contain an origin of DNA replication that functions in yeast, so that the plasmid is maintained extrachromosomally, as a circular episome. Integrating vectors do not contain such an origin and therefore require insertion into a yeast chromosome to be stably maintained.

Both types of plasmids can be introduced into yeast cells by standard transformation methods. Since successful uptake and establishment of plasmid DNA by competent yeast cells is a relatively rare event ($<10^{-3}$), a selection mechanism is required to allow identification of transformants.

Most commonly, selection is accomplished by introducing auxotrophic mutations into the recipient yeast strain. The commonly used mutations are ura3, leu2, trp1, and his3. The plasmid of interest bears a wild type copy of one of these genes. Since the wild type copy on the plasmid is dominant to the host chromosomal allele, selection for cells that receive the plasmid is easily accomplished on a minimal medium lacking the nutrient that is required by the auxotrophic host cell.

There have also been reports of the use of antibiotic resistance to select transformed cells. Replicating vectors have been described that are based on the sensitivity of most Saccharomyces strains to the commercially available neomycin analog, antibiotic G418: Jimenez et al. (1980) Nature 287, 869: Hollenberg (1982) in Current Topics in Microbiology and Immunology. Hofschneider et al., eds. (Springer-Verlag NY); Webster et al. (1983) Gene 26, 243. Webster et al. also describe an integrating plasmid vector which could not be directly selected for by resistance to G418. These vectors contain a gene, called kan$^r$, neo$^r$, or G418$^r$ from the bacterial transposon Tn903, and a yeast origin of replication: the bacterial gene is preceded by its native bacterial promoter.

Another replicating vector has been described which contains the gene for resistance to the antibiotic hygromycin B under the control of a yeast promoter; Gritz et al. (1983) Gene 25, 178.

Beer brewing using yeasts, e.g., members of the genus Saccharomyces, requires the presence of mono-, di-, or tri-saccharides in the fermentation culture medium ("wort"), which the yeasts metabolize in the production of ethanol, $CO_2$ and other metabolites. After yeast fermentation, starches and complex oligosaccharides (those larger than three glucose units) remain soluble but unmetabolized. These oligosaccharides, which are flavorless and colorless, add only to the caloric content of beer.

The production of low starch ("light") beer requires removal of some of the unmetabolized soluble starch and complex oligosaccharides present in the wort that normally remain in the beer after fermentation by yeast. Several methods have been used to reduce the content of starch and complex oligosaccharides in low calorie beer:

1) Passing the wort over an immobilized enzyme, glucoamylase, which is capable of breaking down starch and complex oligosaccharides.

2) Addition of soluble glucoamylase to the wort prior to or during fermentation.

3) Prolonging the mashing process, during which endogenous barley amylases degrade starch.

4) Adding malt flour to the wort during fermentation.

5) Substituting fermentable sugars, such as corn syrup, for various amounts of the starch derived from cereal grains.

6) Diluting the final product with water.

SUMMARY OF THE INVENTION

In general, the invention features a vector including a gene for resistance to an antibiotic otherwise capable of killing a host yeast cell, the gene being transcribed from a yeast promoter sequence or synthetic promoter sequence, the vector being capable of being integrated into a chromosome of the host yeast cell and directly selected for.

A gene heterologous to the host yeast cell (i.e., a non-yeast gene, a modified gene, a gene from a different yeast strain, or a homologous gene from a different chromosomal location) can be inserted into the vector, and the vector used to transform the host cells; transormants are selected on the basis of antibiotic resistance.

In preferred embodiments, the vector also includes a sequence which is homologous with a sequence (a "target" sequence) of a host chromosome, to facilitate integration. Preferably, the homologous sequence is separate from the control sequence which controls the antibiotic resistance gene, and preferably the target is a region where the metabolism of the host cell will not be interfered with.

In other preferred embodiments, the heterologous gene encodes an enzyme, e.g., glucoamylase (which enables the generation of glucose from starch by the yeast cell), and the host cell participates in a process, e.g., the production of dough, which employs a product of the metabolism of the cell, e.g. carbon dioxide.

In other preferred embodiments, the antibiotic resistance gene and the heterologous gene are under the control of different promoters, the promoter controlling the hetrologous gene preferably being the more highly expressed of the two. The preferred integration method is one which results in the depositing of the heterologous gene in the host yeast cell chromosome, to the exclusion of much of the remainder of the vector DNA, providing greatly increased stability. Exclusion of this DNA also eliminates a potential source of interference with a characteristic, e.g., flavor, of the end product.

In another aspect, the invention features a replicating vector which includes a gene for resistance to G418, which gene is under the control of a yeast control sequence.

The integrating vectors of the invention provide stability over generations of host divisions in the absence of selection, an important advantage in industrial fermentation processes; replicating vectors can be lost from yeast cells at rates up to 1% to 5% per generation. Stable maintenace of integrated sequences over generations obviates the addition of toxic antibiotics to the fermentation medium to exert selective pressure to maintain the sequences. The vectors of the invention also function well in yeast, by virtue of the yeast promoter sequence controlling the gene for antibiotic resistance. Furthermore, since industrial yeast strains are usually diploid or polyploid (as opposed to haploid laboratory strains), introduction into them of auxotrophic mutations (used for selection of transformants in haploid strains) is difficult. The use of antibiotic resistance in an integrating vector permits selection of stable transformants in any yeast strain, regardless of number of chromosomes or the presence or absence of specific mutations.

Introduction of geners encoding heterologous enzymes into industrial yeast strains using the vectors of the invention will facilitate the production of such products as alcohol, which ordinarily relies on sugars to feed the yeast. An enzyme such as glucoamylase will enable the yeast to break down starch from inexpensive sources such as tapioca and potatoes to yield glucose, which can be fed on by the yeast. Similarly, bread-making can be made cheaper when starch (flour) rather than sugar is used as the primary energy source.

In another aspect, the invention features a diploid or greater ploidy yeast cell transformed with DNA encoding glucoamylase, the yeast cell being capable of producing enzymatically active glucoamylase.

In preferred embodiments, the yeast cell is diploid, triploid, tetraploid, or aneuploid; the glucoamylase-encoding DNA is introduced via a plasmid capable of integrating into a chromosome of the host yeast cell via a sequence on the plasmid homologous with a region of a chromosome of the host cell; the plasmid is integrated into more than one such homologous region-containing chromosome in the host cell; the glucoamylase-encoding DNA is substantially identical to glucoamylase coding sequences of DNA of the mold *Aspergillus niger;* and the host yeast cell is a beer brewing strain (most preferably lager) used to brew beer, (e.g., light beer) or is a spirits (e.g., whiskey or fuel-ethanol) distilling or bread-making strain.

The plasmids of the invention can be integrated in a way which results in the plasmid DNA remaining substantially intact in the host chromosome, or in a way which results in the jettisoning of unwanted plasmid sequences, e.g., *E. coli* sequences. In both cases, the plasmid includes a region homologous with a region of the host chromosome. In the jettisonning case, the plasmid, prior to transformation, is linearized (as it is also in the non-jettisonning case), and the homologous sequence of the host chromosome has a first and a second end and the plasmid includes a first and a second sequence, respectively homologous with the first and second ends, which sequences are separated from each other by a region of partial non-homology which includes the DNA encoding glucoamylase, a third sequence homologous with the corresponding region of the host chromosome, DNA encoding a selectable trait, and DNA encoding a screenable trait.

In another aspect, the invention features an improved method of transforming diploid or greater ploidy yeast cells with plasmid DNA involving contacting the cells and the plasmid DNA under transforming conditions, plating the cells on a porous support, and then selecting transformants, the temperature of the yeast cells being maintained below 40° C. for the entire period during the transforming and selecting steps.

The invention makes possible the use of modified forms of the yeast strains normally used in brewing to degrade complex oligosaccharides to produce low-calorie light beer, obviating the addition of exogenous enzyme or diluents, or the use of additional or longer brewing steps, while preserving the distinctive flavor characteristics of the beer imparted by the brewing strain. The invention also makes possible an increased yield of distilled ethanol from the fermentation of grain or other starch-containing mashes. The invention also reduces the sugar requirement in leavening of bread by yeast.

Other enzymes can facilitate commercial fermentation processes in other respects. For example, in wine-making, insertion of the gene for malolactic enzyme or malate permease will permit host yeast cells to metabolize malic acid from grapes, thus inhibiting spoilage of the wine by removing malic acid, which is otherwise fed on by spoilage bacteria.

Other features and advantages of the invention will be apparent from the following description of preferred embodiments thereof, and from the claims.

DESCRIPTION OF THE PREFERRED EMBODIMENTS

The drawings will first briefly be described.

DRAWINGS

In the figures, the following abbreviations are used for restriction endonuclease cleavage sites: A, XbaI; B, BamHI; Bs, BssHII; E, EcoRI; H, HindIII; K, KpnI; L, BclI; M, SmaI; P, PstI; PI, PvuI; PII, PvuII; S,SalI; Sp, SphI; T or TII, SstII; U, StuI; X, XhoI. (A) denotes the position of a former XbaI site located about 3 kilobases away from the 5′ end of the HO gene. This site was destroyed and replaced by a SalI site in the construction of pRY253. (PII) represents a former PvuII site similarly lost or destroyed during plasmid construction. Complete genes or gene fusions are shown by boxes. The abbreviations for the genes are as follows: amp$^r$, ampicillin resistance; G418$^r$, antibiotic G418 resistance; HO, homothallism; CYCl, iso-1-cytochrome c; URA3, orotidine-5′-monophosphate decarboxylase; GAL1, galactokinase; lacZ, beta-galactosidase; CA, *A. niger* pre-glucoamylase; TPI, triose phosphate isomerase. The concentric arrows inside the circles indicate segments of DNA having origins other than pBR322; the extent of these sequences is indicated by the arrowheads and the source is indicated by the labels, and no arrow indicates *E. coli* origin. Other abbreviations are: kb, kilobase pairs; ori, *E. coli* origin of replication.

In FIG. 9a–FIG. 9e, the following abbreviations are used: X, any gene or DNA sequence to be integrated into a yeast chromosome and expressed: S, a cloning site (for example: a restriction endonuclease site) into which gene X is inserted: L, a site (for example, a restriction endonuclease site) for linearizing the vector within the target sequence, "T⇌ or "Target"; R, a site, not necessarily specific, where recombination between homologous vector-derived and chromosome-derived target sequences occurs. An apostrophe designates half of a site (such as S or L) that is separated from its other half by cleavage, by insertion of an intervening DNA sequence, or by integration into a chromosome. A subscript of V or C designates sites or portions of sites that are derived from the vector or chromosome, respectively. Other abbreviations are as in FIG. 1 and 6–8.

Figure 6:
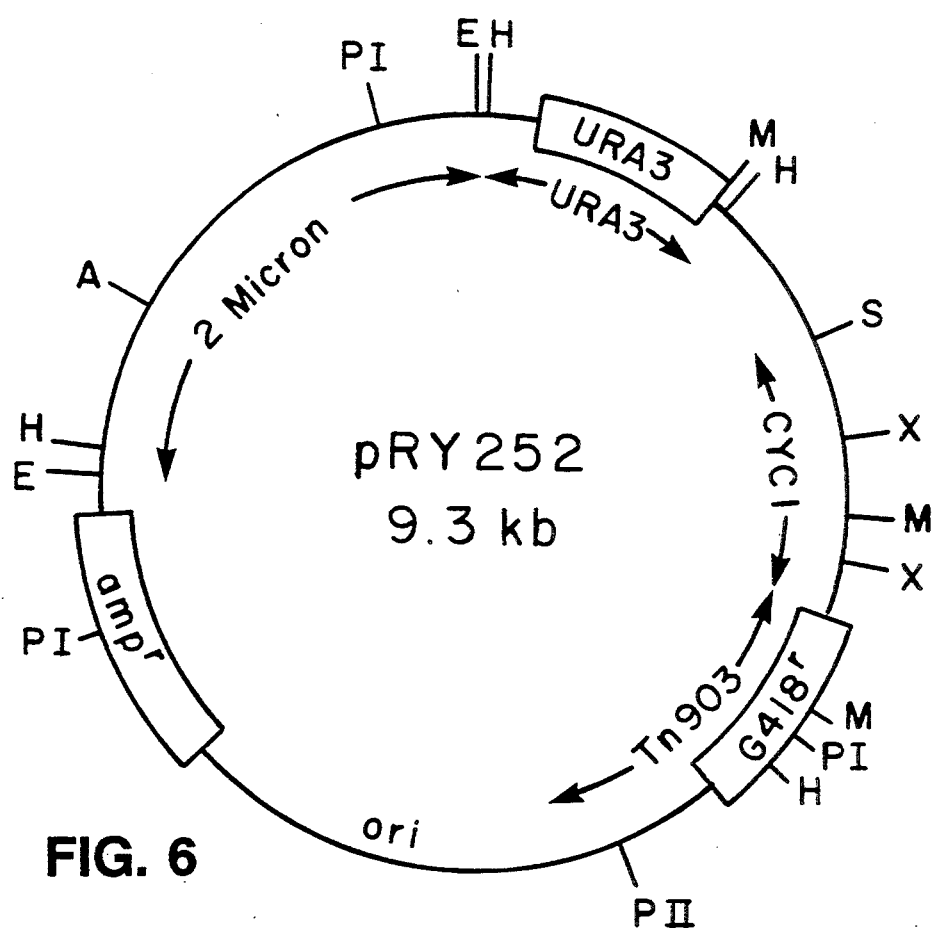
FIG. 6 is a diagrammatic representation of a replicating vector of the invention.

Referring to FIG. 6, replicating plasmid vector PRY252 is composed, beginning at the 12 o'clock position of the drawing and moving clockwise, of sequence E-H, a small piece of DNA from the *E. coli* plasmid pBR322; sequence H-H, which includes the yeast URA3 gene (one of the genes required for the ability to grow on uracil-deficient media; this gene is an unnecessary artifact in the plasmid which was originally inserted to provide a comparative selection means); sequence H-S, another piece of pBR322; sequence S-(PII), which includes the yeast CYC1 (cytochrome c) promoter and most of the gene for resistance to G418 from the bacterial transposon Tn903 (the non-essential N-terminal region is not included); sequence (PII)-E, including the *E. coli* origin of replication from pBR322 and the amp$^r$ gene for selecting transformants in *E. coli;* and sequence E-E, the yeast origin of replication from a yeast 2 micron circle.

Figure 7:
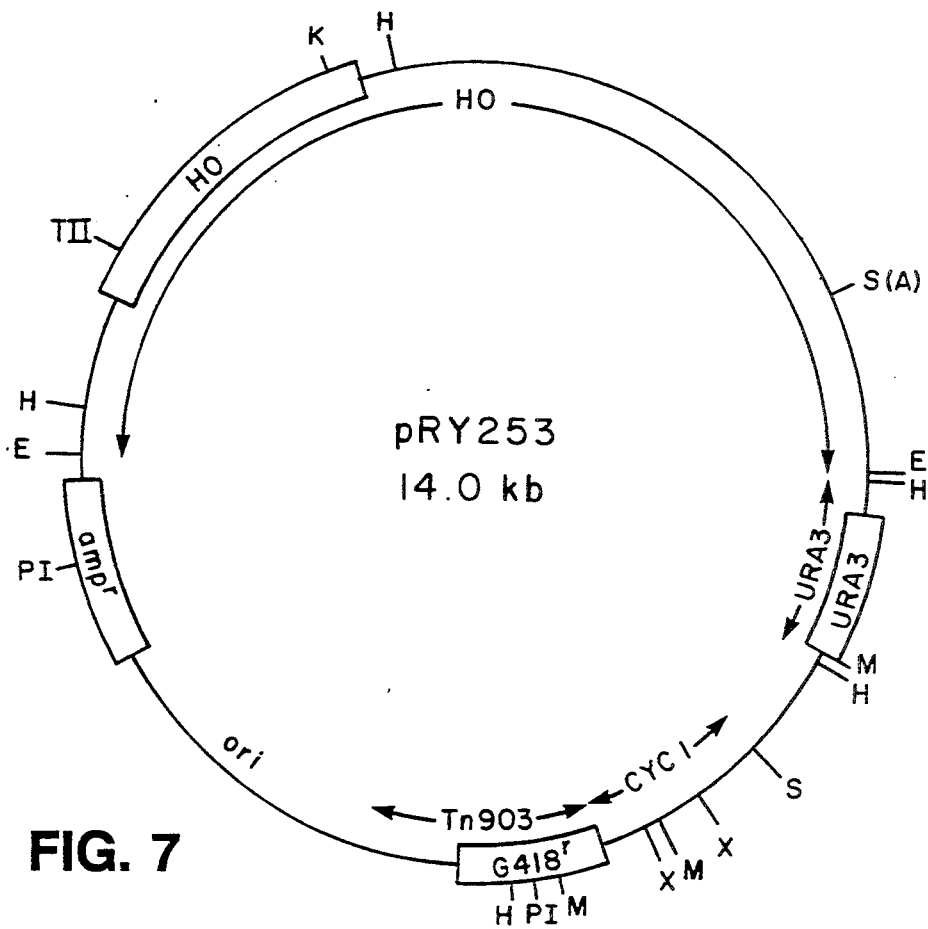
FIGS. 7 and 8 are diagrammatic representations of integrating vectors of the invention.

Referring to FIG. 7, integrating plasmid vector pRY253 is derived from pRY252 in that the yeast origin of replication sequence is replaced by a 7.0 kb EcoRI fragment of *S. cerevisiae* containing the HO (homothallism) gene, including site K for insertion of a desired heterologous gene.

Figure 1:
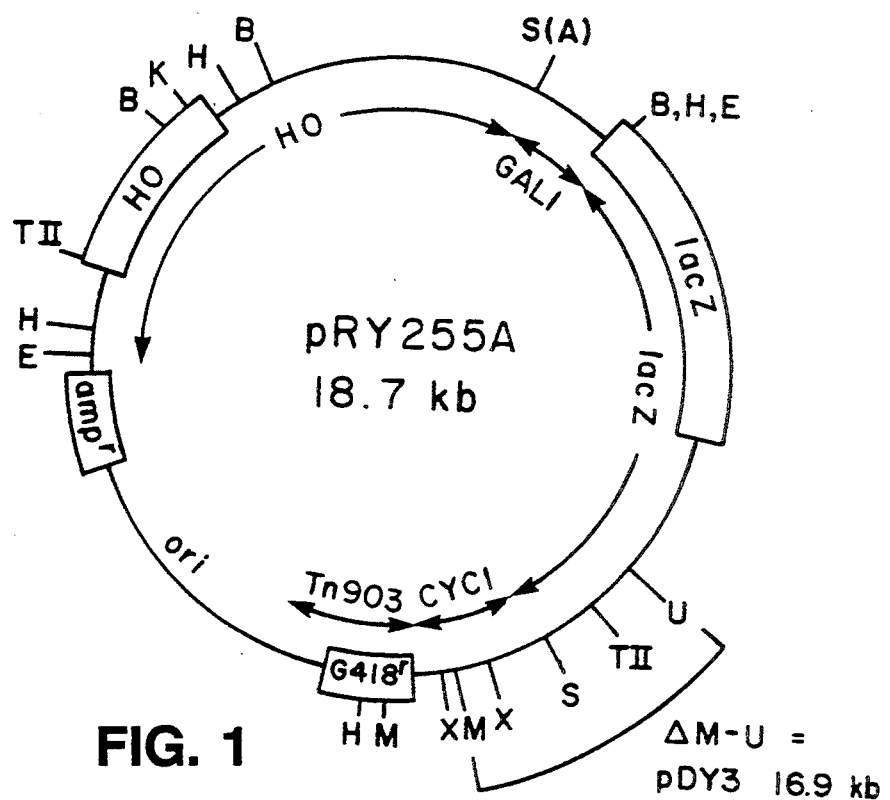
FIGS. 1 and 3 are diagrammatic representations of plasmids used in the construction of the plasmid of FIG. 2.
Figure 8:
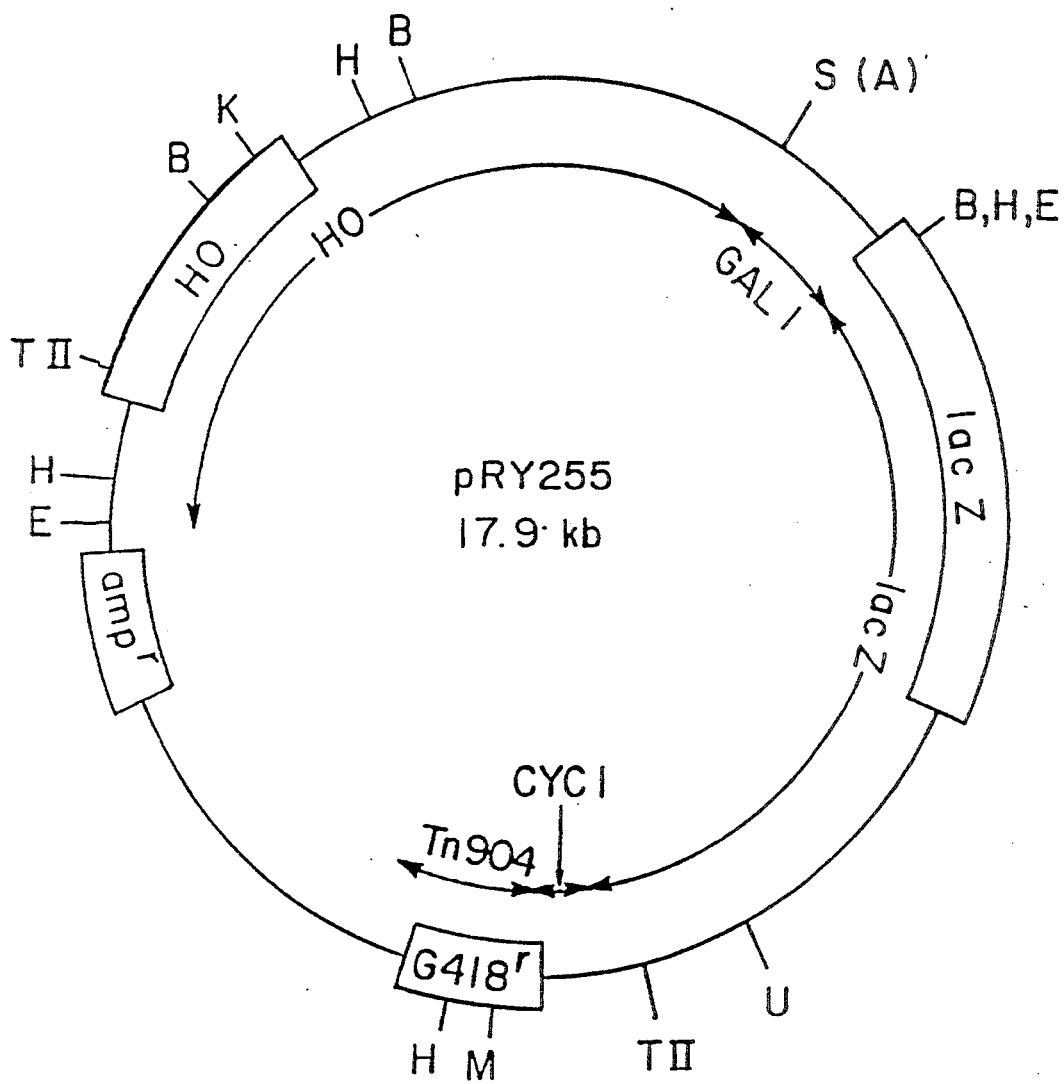

Referring to FIG. 8, integrating plasmid vector pRY255 is derived from pRY253 in that a 3.3 kilobase SalI to XhoI fragment extending from one end of the HO insert to the beginning of the CYC1 promoter sequence and containing the URA3 gene has been replaced with a 6.0 kilobase XhoI to SalI fragment containing a gene fusion of the yeast GAL1 gene and the *E. coli* lacZ gene. Referring to FIG. 1, pRY255A is similar to pRY255, in that it is also derived from pRY253, in that the 6.0 kilobase XhoI to SalI fragment containing the GAL1-lacZ fusion is substituted for the 2.5 kilobase SalI fragment of pRY253.

Referring also to FIG. 1, pDY3 was derived from pRY255A by deleting the 1.8 kilobase region between a StuI site and the SmaI site upstream from the CYC1 promoter.

pRY255A and pDY3 can be used in substantially the same way as pRY255, as described below. In addition, in pDY3, an SstII site near the 3' end of the HO gene is unique on the vector, making it a more convenient site for linearization of the vector.

Figure 9A:
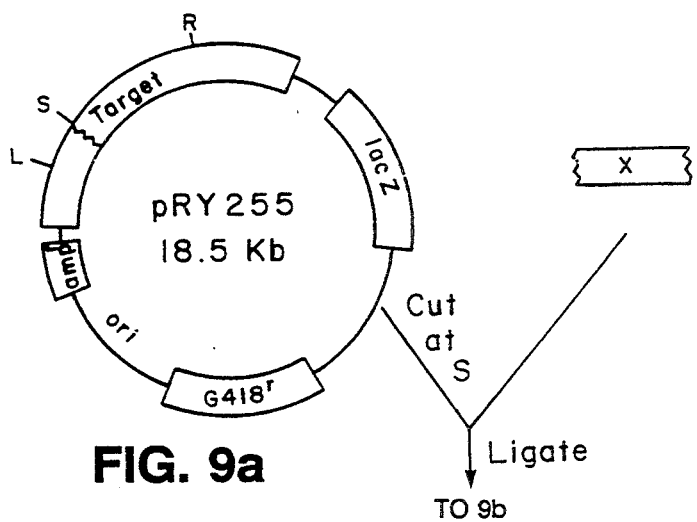
FIG. 9a–FIG. 9e is a diagrammatic representation of a mechanism by which an integrating vector is integrated into a host yeast chromosome.
Figure 9B:
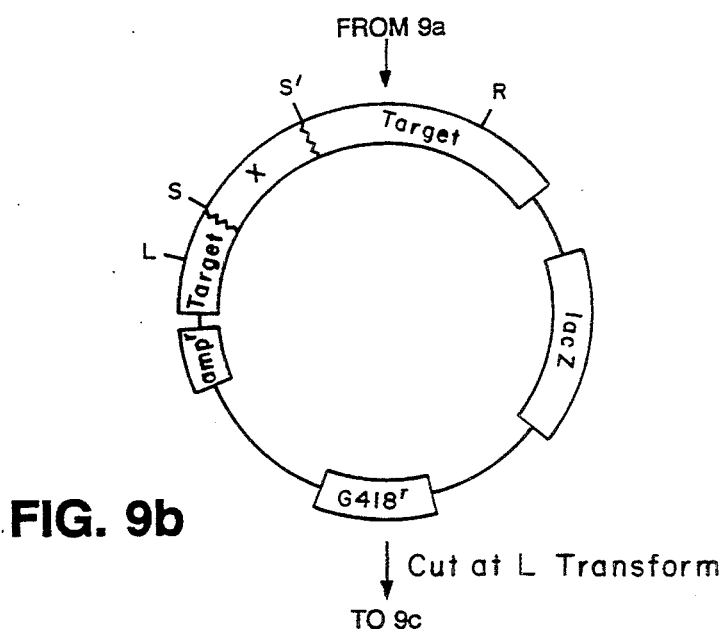
Figure 9C:
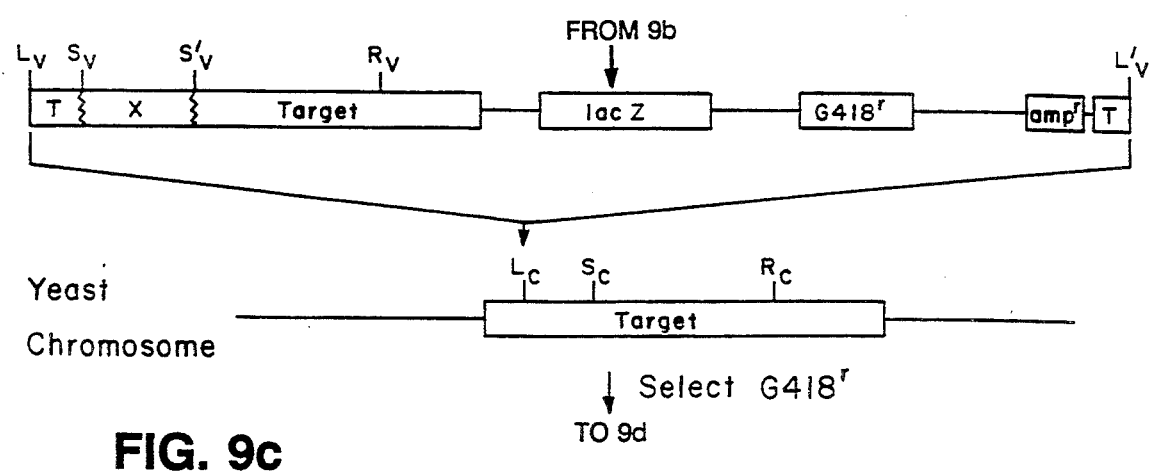
Figure 9D:
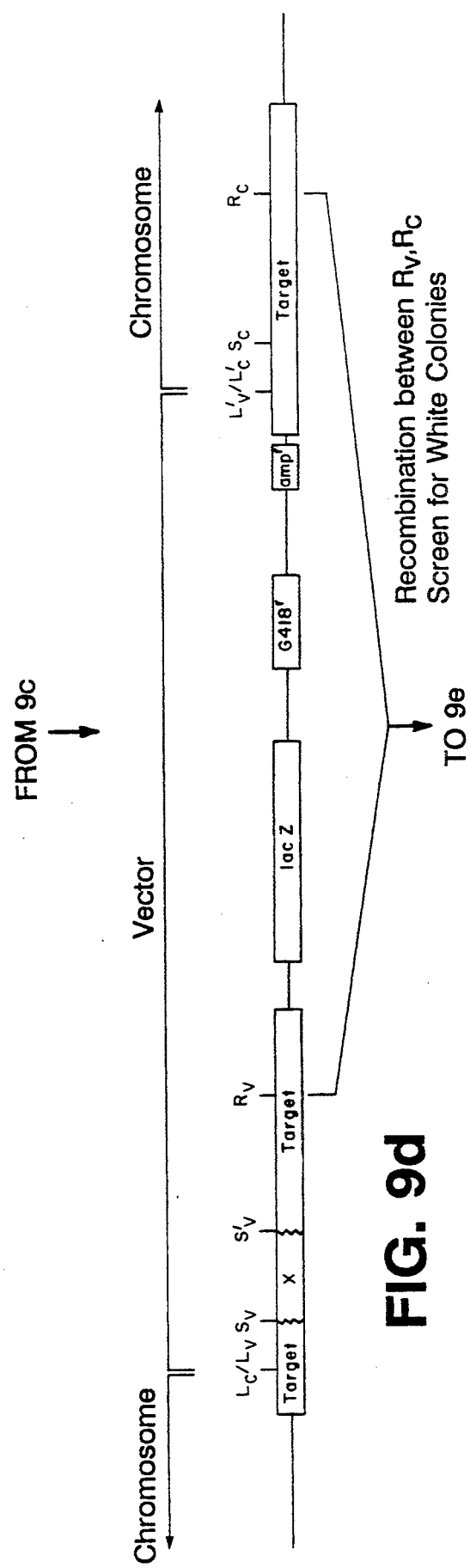
Figure 9E:
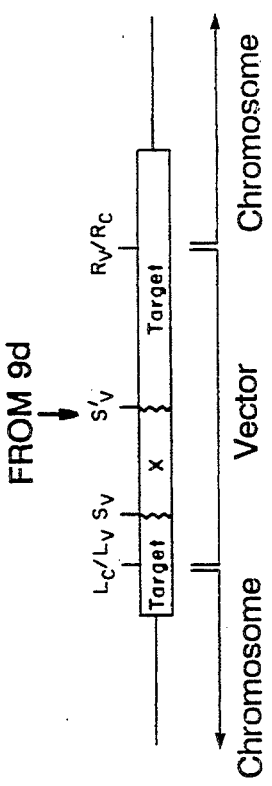

Referring to FIG. 9b, plasmid pRY257 will contain a gene X for a desired heterologous protein, e,g., glucoamylase or interferon, inserted at site S in plasmid pRY255. A plasmid constructed by inserting a glucoamylase-encoding gene into pDY3 is described below.

The plasmids illustrated in FIGS. 1, 6–8 were made using conventional recombinant DNA methods and publicly available materials.

Plasmids pRY253, pRY255, pRY255A, and pDY3 were derived from replicating plasmid pRY252 which, briefly, was constructed as follows.

The URA3 gene was inserted into plasmid pBR322 as illustrated, and then the origin of replication from the endogenous yeast 2 micron circle, without the three genes normally accompanying it, was inserted. The vector is able to replicate in host yeast cells without containing these three genes, two of which encode proteins essential for replication, because host yeast cells already contain the endogenous 2 micron circle encoding those proteins (Botstein et al. (1979) Gene 8, 17).

The CYC1-G418$^r$ fusion portion of the plasmid was constructed by fusing the XhoI site near the 5' end of the G418$^r$ gene of transposon Tn903 (described in Oka et al. (1981) J. Mol. Biol. 147, 217) to the BamHI site following the CYC1 promoter and the 5' end of the CYC1 coding sequences of plasmid pLG669 (described in Guarente et al. (1981) PNAS USA 78, 2199) after rendering both ends flush with mung bean nuclease. The DNA sequence of this fusion junction is (CYC1) . . . TAAAT-TAATAATGACCGGGCCG . . . (G418$^r$). The arrow shows the point of fusion.

Plasmids pRY253, pRY255, pRY255A, and pDY3 were constructed from pRY252 by making the gene fragment substitutions and deletions shown in the Figures. Plasmid pRY257 can be constructed by inserting a gene X for a desired protein at site S of pRY255, within the HO gene, so that there are portions of the HO gene on either side of gene X, as shown in FIG. 9b.

The vectors of the invention can be used in any useful process in which host yeast cells express a desired heterologous gene. The desired heterologous gene can be inserted using conventional recombinant DNA techniques, e.g., as described in Maniatis et al. (1982) *Molecular Cloning: A Laboratory Manual*, Cold Spring Harbor Press, Cold Spring Harbor, N.Y., hereby incorporated by reference.

pRY253; pRY255, pRY255A, and pDY3 can also be used to delete genes from wild type yeast strains. For the deletion of genes, the HO portion of the vectors becomes irrelevant. Deletion of a gene or a portion of a gene can be accomplished as follows:

1. Clone the gene to be deleted with some adjacent sequences on both sides of the gene.

2. Create a deletion of the cloned gene in vitro, leaving some adjacent sequences from both ends of the gene.

3. Place the deletion-containing DNA at an appropriate location in one of the integration vectors described herein.

4. Linearize the vector at a point in one of the sequences adjacent to the deletion, and perform integrative transformation, selecting for G418 antibiotic resistance.

5. Grow a stable transformant for 20 to 40 generations non-selectively, and screen for vector jettisonning events either by loss of blue colony color on Xgal (see below) indicator plates, or by replica plating to G418-containing plates.

6. Screen among colonies that have jettisonned the vector for those that retained the deleted version of the gene by Southern blotting.

The vectors are particularly useful in industrial yeast strains used in the production of end products such as wine, bread, beer and distilled spirits which involve carbohydrate fermentation. In such strains, the vectors either provide the capacity to produce a desired protein such as an enzyme, or advantageously delete a gene encoding an unwanted protein.

Transformation

Transformation of host yeast cells is carried out using any suitable technique. Yeast cells were transformed with vectors of the invention as follows.

Laboratory yeast strain DBY 745 (described in Guarente et al. (1981) PNAS USA 78, 2199); a Carlsberg$^R$ brewing strain (isolated from unpasteurized beer); Fleischman's$^R$ baking yeast (purchased at a supermarket); and a Bordeaux wine yeast (ATCC 42928) were grown in a standard rich medium, YEP-D, spheroplasted with glusulase, and exposed to plasmid DNA by standard methods of yeast transformation, as described in Sherman et al. (1981) Methods in Yeast Genetics (Cold Spring Harbor Laboratories Press, Cold Spring Harbor, N.Y.). Integrating plasmid pRY253 was linearized by restriction endonuclease digestion, at a unique SstII site near the 3' end of the HO gene, and pRY255 was linearized at a unique KpnI site near the 5' end of the HO gene, prior to transformation, in order to direct integration at the HO locus. Replicating plasmid pRY252 was not linearized.

After exposure to the plasmids, $10^8$ spheroplasts were grown in YEP-D plus 1.0M sorbitol for 30 minutes at 30° C. and then plated in 6 ml of warm 3% agarose containing YEP-D over 20 ml of 2% agar, YEP-D, 1.0M sorbitol, and 70 mM potassium phosphate. pH 7.0. After 10 minutes of cooling at room temperature, another 4 ml of warm 1% agar, YEP-D, 1.0M sorbitol was layered over the top agar. The cells were then allowed to grow at 30° C. for 6 generations, corresponding to 8 hours for DBY 745, 9 hours for Carlsberg, 7 hours for the wine yeast, and 6 hours for Fleishman's. After this "growing out" period, 0.6 ml of a sterile solution of antibiotic G418 at 25 mg/ml was spread over the agar surface and allowed to dry in a sterile hood. The plates were then incubated for 2–5 days at 30° C., after which time colonies appeared out of a background of untransformed cells. Several of these colonies were toothpicked onto fresh YEP-D plates containing 500 μg/ml G418. Cells that were successfully transformed gave rise to visible colonies within 24 hours, while untransformed cells did not. A summary of these results is given in Table 1, below.

TABLE 1

Number of G418 resistant transformants per $10^8$ competent cells from 1 μg of plasmid DNA.

| Strain | None | pRY252 | pRY253[a] | pRY255[b] |
|---|---|---|---|---|
| DBY 745 | 0 | 5,200 | 890 | 800 |
| Carlsberg | 0 | 260 | 13 | 7 |
| Wine Yeast (ATCC #42928) | 0 | 450 | 30 | 21 |
| Fleischman's | 0 | 510 | 22 | 17 |

[a] linearized with SstII prior to transformation.
[b] linearized with KpnI prior to transformation Transformants obtained from the integrating plasmids pRY253 and pRY255 were shown to contain stably integrated plasmids by growing isolated transformants for 10 to 20 generations non-selectively in YEP-D and showing that reversion to G418 sensitivity occurred at a rate less than $10^{-3}$. Transformants containing pRY255 gave blue colonies on plates containing galactose as the sole carbon source. 70 mM potassium phosphate buffer, pH 7.0, and Xgal indicator dye (5'-bromo-4'-chloro-3'-indoyl-beta-D-galactoside).

Jettisoning of Vector Sequences

Plasmid vector pRY257 can be linearized and used to transform host yeast cells, as described above for plasmids pRY253 and pRY255. As described above. transformants are selected on the basis of antibiotic resistance (FIG. 9a–FIG. 9e).

Following this selection, as shown in FIG. 9 a further step can be taken to jettison unnecessary portions of the vector which might adversely affect transformant stability, adversely affect the taste or any other important property of the end product, or waste metabolic energy. In effect, this screening step "deposits" the desired gene in the host chromosome, while excluding extraneous DNA. The exclusion of this extraneous DNA increases transformant stability by eliminating tandem repeat sequences which could cause undesirable recombination events resulting, for example, in loss of the desired heterologous gene. Also, elimination of the gene for antibiotic resistance can be an advantage if for some reason it is anticipated that the use of the antibiotic to kill the yeast may become necessary. Finally, elimination of all *Escherichia coli* derived sequences from the transformed yeast may simplify governmental regulatory clearance for use of the organism.

The screening depends on the presence in the vector of a gene encoding a screenable trait; in pRY257, this is the *E. coli lacZ* gene which encodes beta-galactosidase. Yeast colonies that express this gene turn blue on an appropriate indicator petri plate containing a colorimetric indicator dye such as Xgal. Thus to select transformants in which a portion of the vector DNA, including the *lacZ* gene, has been jettisoned, transformants are plated onto an indicator plate, and those colonies remaining white on the plates selected as the transformants, or descendants of transformants, not retaining the *lacZ* gene.

FIG. 9a–FIG. 9e illustrates the jettisoning mechanism. In some transformants there will be a cross-over event between vector sequences homologous with chromosome sequences (see FIG. 9d). This cross-over event causes the looping out and deletion of the region of the vector between the homologous sequences (see FIG. 9e). If desired heterologous gene X (encoding, say. glucoamylase) is outside this region, it remains deposited in the chromosome. The frequency of this type of event can be increased relative to that of other unwanted events (such as looping out of the entire plasmid including the deposited gene) by placing the deposited gene nearer to the end of the target sequences containing the linearization site than to the end of the target sequences that contain the "looping out" site.

The desired looping out event can be distinguished from undesired events by screening among White colonies for those that maintain gene X. This can be done either by a functional assay for the product of gene X (e.g., in the case of glucoamylase, halos on starch-containing plates), or by direct assay for the presence of gene X by Southern blotting techniques. The two screenings can be carried out at once, e.g., by using a medium containing both Xgal and starch.

Plasmid Components

As is mentioned above, plasmids of the invention useful for the transformation of yeast cells for the fermentation of starches in the production of, e.g. light beer, include several components, now discussed in more detail.

DNA Encoding Glucoamylase

The glucoamylase-encoding DNA used to transform the yeast cells of the invention can be derived from many sources; the most preferred DNA is the glucoamylase gene of the bread mold *A. niger*. "Glucoamylase" refers to any exo-enzyme capable of degrading glucose-containing oligosaccharides more than three units in length. As will be described in more detail below, it is not necessary that the enzyme include the entire product of the structural gene which encodes the naturally occurring enzyme; we have shown that a less than complete gene product, encoded by a less than complete structural gene, exhibits glucoamylase activity. In addition, some microorganisms produce more than one form of glucoamylase. For example, *A. niger* is known to produce two forms of secreted glucoamylase, called GI and GII (Boel et al. (1984) EMBO J. 3, 1097). Form GI results from the splicing out of four introns at the mRNA level; form GII results from the splicing out of the same four introns plus an addition fifth intron of 169 bases located near the 3' end of the transcript.

Regulatory DNA

In order for the glucoamylase-encoding DNA to be adequately expressed in the host yeast cells, transcription of the DNA must be under the control of a promoter sequence which is recognized by the yeast transcriptional machinery. Preferred are promoter sequences isolated from or substantially identical to yeast promoters, e.g. the promoter naturally controlling transcription of the *S. cerevisiae* triose phosphate isomerase ("TPI") gene.

In addition to a promoter sequence, there is preferably, downstream from the glucoamylase-encoding DNA, a suitable transcription terminator, which is also preferably derived from a yeast cell such as *S. cerevisiae,* and preferably, but not necessarily, derived from the same gene as the promoter used.

Integration Sequence

It is preferred that the vector of the invention be capable of integration into a chromosome of the host yeast cell. This is preferably accomplished by means of a sequence on the vector which is homologous with a sequence (a "target" sequence) of a host chromosome. Preferably, the homologous sequence is a region in which integration will not adversely affect the metabolism and flavor characteristics of the host cell. A preferred target region on the host chromosome is the homothallism (HO) gene, which is advantageously large, and is not related to flavor characteristics of the host yeast.

Integration provides stability over many host cell generations in the absence of selection, an important advantage in industrial fermentation processes and brewing; autonomously replicating plasmids can be lost from yeast cells at rates up to 1% to 5% per generation.

Selectable Marker

Because transformation of yeast cells with plasmids is a relatively rare event, vectors of the invention preferably contain a DNA region which encodes a selectable marker protein for the identification of transformants. This marker protein can be any protein which can be expressed in host yeast cells and which enables the phenotypic identification of yeast cells which express the protein. Preferred marker proteins are proteins which confer resistance to one or more antibiotics, e.g., antibiotic G418. Transformants are those cells able to grow in the presence of the antibiotic.

Host Yeast Cells

The yeast cells transformed and cultured according to the invention are diploid or greater ploidy strains used in beer and ale brewing, or in distilled spirits (e.g., whiskey) and bread making. Generally, *S. cerevisiae* strains, which are "top fermenting" strains, are used in making ales, while *S. uvarum* strains, which are "bottom fermenting" strains, are used in making lager beer, including light beer. Beer and ale brewing strains often are tetraploid, while whiskey and other distillery, and bread strains, are often diploid. Other industrial strains are aneuploid, i.e., of a ploidy not an exact multiple of haploid.

The yeast strains used in the invention are those which already are capable of metabolizing simple sugars to produce the desired ale, beer, whiskey, other distilled spirit, or bread product with the characteristic flavor of the product, and which only lack, prior to transformation according to the invention, the ability to metabolize complex oligosaccharides and starches. Many suitable yeast strains are publicly available.

As already mentioned, the invention permits the production of light beer or ale without additional steps to remove oligosaccharides. In the case of whiskey and other distilled spirits, and bread, the invention permits the use of lower-cost starting materials, i.e. starch rather than sugar, while retaining the desirable flavor characteristics of the fermenting strain.

Plasmid Structure

Figure 2:
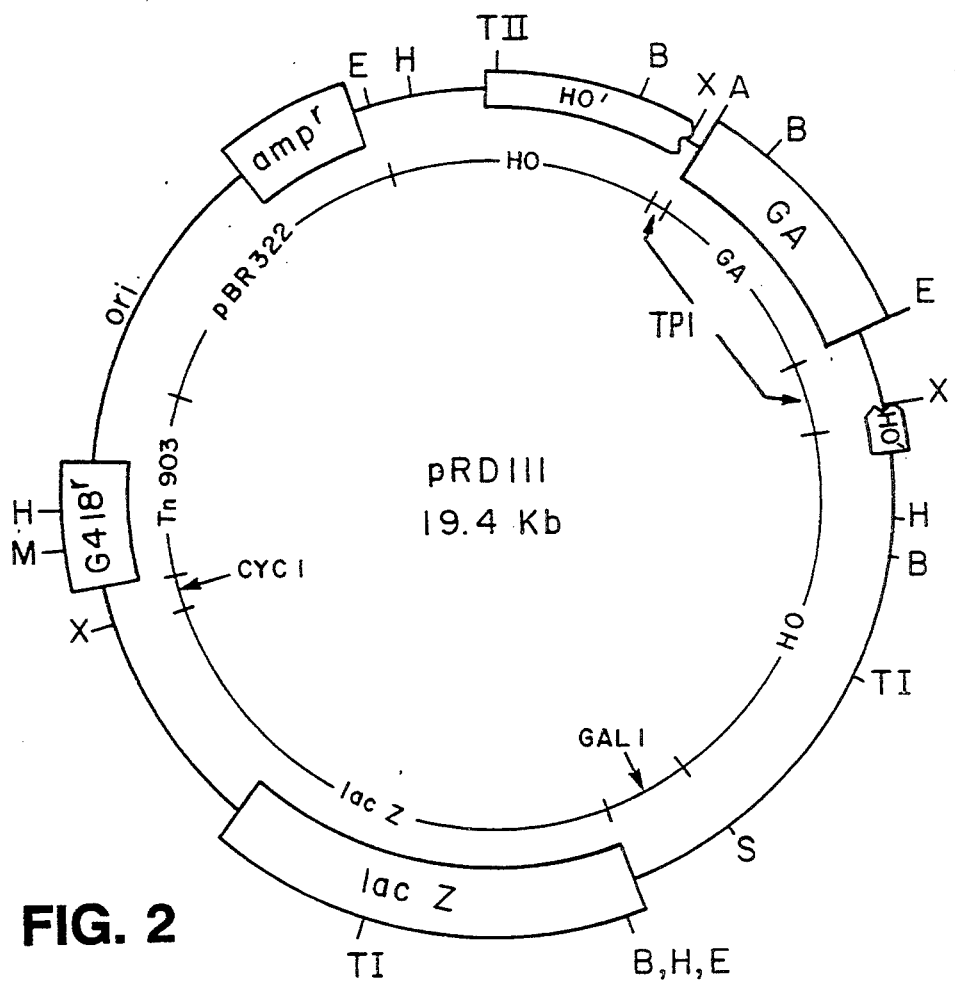
FIGS. 2 and 5 are diagrammatic representations of plasmids of the invention.

Referring to FIG. 1, plasmid pDY3, into which the *A. niger* preglucoamylase gene was inserted, is composed, beginning at the one o'clock position and moving clockwise, of an XhoI to StuI fragment containing a gene fusion of the yeast GAL1 gene and the *E. coli lacZ* gene; a SmaI to PvuII fragment including the yeast CYC1 promoter and most of the gene for resistance to the antibiotic G418 from the bacterial transposon Tn903 (the non-essential N-terminal region is not included); a PvuII to EcoRI fragment including the *E. coli* origin of replication from pBR322 and the amp$^r$ gene for selecting transformants in *E. coli;* and an EcoRI to XbaI fragment of *S. cerevisiae* containing the HO gene, including a KpnI site for the insertion of the *A. niger* preglucoamylase gene. FIG. 2 illustrates pRD111, which contains that gene. In FIG. 2, the source of all DNA is indicated on the inner concentric circle.

Vector Construction

The first step was the construction of pDY3 as described herein, above. The next step was the isolation of the *A. niger* preglucoamylase gene.

Isolation of the A. niger Preglucoamylase Gene

A. niger was grown by shaking 10$^6$ spores per liter at 30° C. in a medium containing, per liter, 7 g Yeast Nitrogen Base (Difco) and 20 g Soluble Starch (Fisher). Mycelium was harvested by filtration after 3 days of growth and total RNA was prepared by the method of Lucas et al. (1977) J. Bacteriol. 130, 1192.

PolyA-containing mRNA was isolated by two passes over oligo-dT-cellulose and used to construct a cDNA library by the standard method of G-C tailing into the PstI site of pBR322 (Maniatis et al. (1982) Molecular Cloning, Cold Spring Harbor Laboratory Press, Cold Spring Harbor, N.Y.). The cDNA library was transformed into E. coli strain YMC9. Single colonies from about 25,000 transformants were screened with a $^{32}$P-labeled synthetic 27 base oligonucleotide probe corresponding to amino acids 259–268 of A. niger glucoamylase as published by Svenson et al. (1983) Carlsberg Res. Commun. 48, 529. The sequence of the 27-mer was:
5'-GCATGCGACGACTCCACCTTCCAGCCC-3'

Twelve clones that hybridized with the probe were characterized. One of them, designated pl-19A, contained a 2,200 base pair insert that was shown by DNA sequence analysis to contain the entire coding sequence for preglucoamylase I, as described by Boel et al. (1984) EMBO J. 3, 1097.

Figure 3:
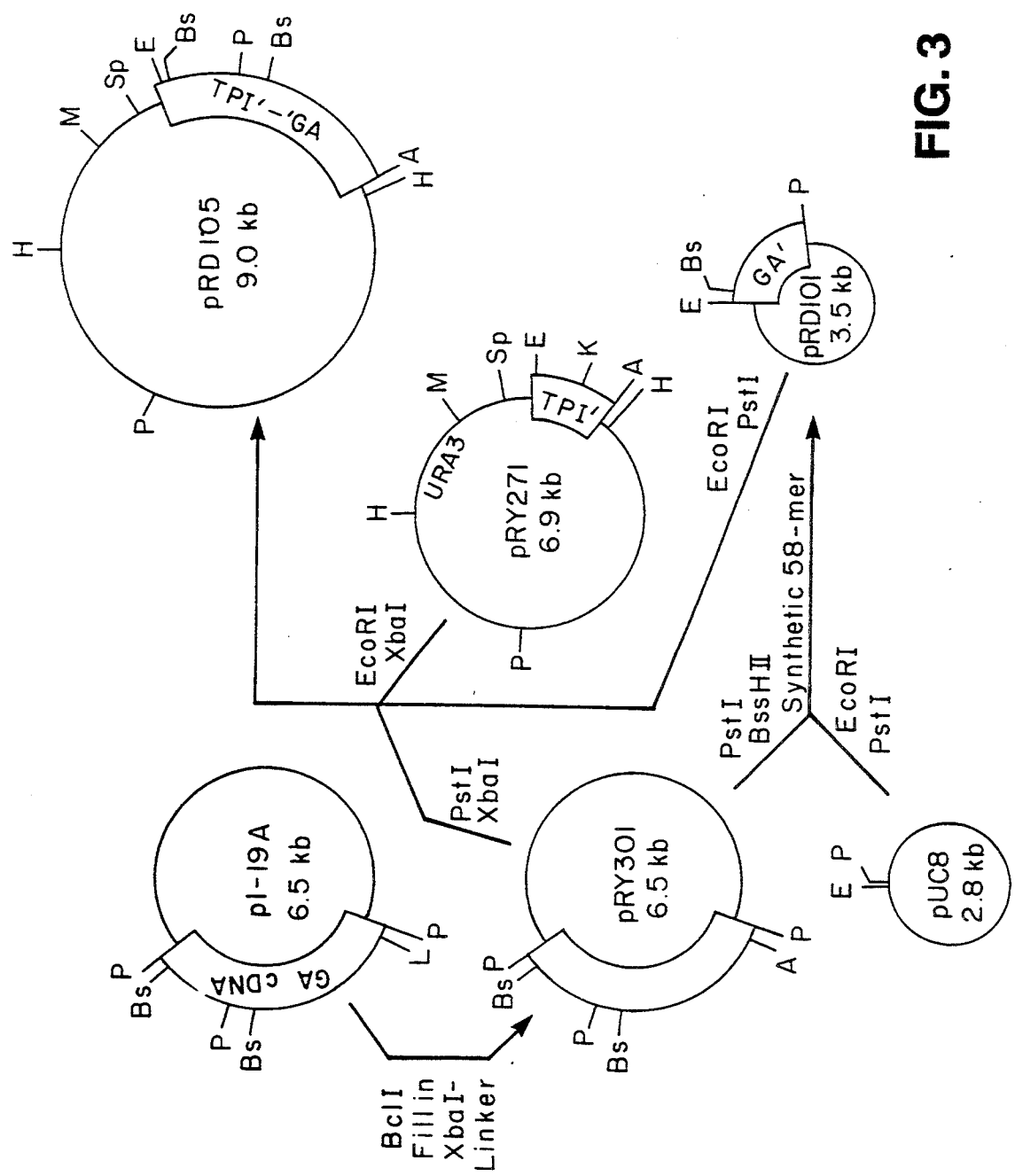

The following constructions and steps are illustrated in FIG. 3.

A unique BclI restriction site was located 54 base pairs downstream from the termination codon of the preglucoamylase I gene in pl-19A. This site was converted into an XbaI site by standard methods (Maniatis et al. (1982), id) to yield plasmid pRY301.

Figures 4, 5:
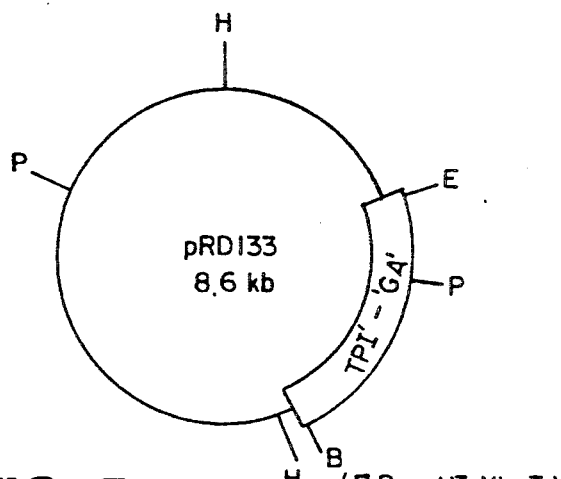
FIG. 4 is the nucleotide sequence of a 58-base segment of synthetic DNA used in the construction of said plasmid.

A BssHII to PstI fragment containing bases 69–746 of the preglucoamylase I coding sequence was cut out of pRY301 and ligated together with a synthetic 58-mer that replaces sequences lost in the subcloning of the BssHII to PstI fragment (FIG. 4) into the EcoRI to PstI backbone of pUC8 (New England Biolabs) to give pRD101.

Construction of Glucoamylase Fusion Gene

Preglucoamylase was expressed as a fusion protein from the S. cerevisiae TPI promoter. The gene coding for the fusion protein contains DNA including the TPI promoter, the first three amino acids of TPI, an EcoRI linker which creates an isoleucine codon, and preglucoamylase I beginning at the leucine at the sixth position. The DNA sequence around the fusion junction is:

```
        Met Ala Arg Ile  Leu Leu ...
      · ATG GCT AGA ATT  CTA CTC
        TAC CGA TCT TAA  GAT GAG
```

The staggered line indicates the EcoRI cleavage site at the fusion junction. The gene fusion was constructed as follows. pRY271 is an expression vector containing an EcoRI linker inserted at codon three of TPI and a natural XbaI site just upstream from the TPI transcription terminator (FIG. 3). Between the aforementioned EcoRI and XbaI sites was inserted two DNA fragments, the EcoRI-PstI piece of preglucoamylase cDNA from pRD101, and the PstI-XbaI piece of preglucoamylase cDNA from pRY301. This yielded pRD105.

The entire gene fusion from pRD105, containing the TPI promoter and terminator, and the TPI-preglucoamylase gene fusion on a SmaI-HindIII fragment, was then transferred by blunt end ligation with XhoI linkers into the KpnI site of pDY3 (FIG. 1), to yield the integrating plasmid pRD111 (FIG. 2).

An additional plasmid, pRD133 (FIG. 5), was constructed which contained a cDNA encoding a protein which mimics GII, described above; construction was as follows. Plasmid pRD105 was cut with BamHI and XbaI to remove the 3' end of the glucoamylase gene. The resulting fragment was ligated with a synthetic linker of the following sequence:

5'—GATCCTAGTAAC
    GATCATTGGATC—5', to yield pRD133. Plasmid pRD133 was designed to encode a protein that is missing the amino acids covering the fifth intron, as well as a several additional amino acids on both sides of the intron. The linker was designed such that no extraneous amino acid sequences were introduced.

Upon transformation into yeast, pRD133 yields a slight increase (about 10%) in glucoamylase activity over pRD105, so yeast strains containing the shortened version of the glucoamylase gene may be preferred in some instances. The shortened version can be easily transferred to the integrating vector pDY3 on a SmaI to HindIII fragment, in a manner analogous to the construction of pRD111 from pRD105 as described above.

An integrating vector containing the shortened version of the glucoamylase gene can also be constructed from pRD111 as follows. pRD111 can be partially cleaved with BamHI under conditions that give an average of one BamHI cut per molecule. Full length linear plasmid can then be separated from circular (uncut) plasmid by standard preparative gel electrophoresis. The isolated linear plasmid can then be cleaved with XbaI and ligated with the synthetic linker described above.

Transformation of Polyploid Brewing Strains

American lager beer strains are more difficult to transform than most other yeast strains. In fact, we found it impossible to transform American lager strains with integrating plasmids using standard procedures such as is described in Webster et al. (1983) Gene 26, 243. Therefore, we devised a new method that is more efficient than standard procedures and that routinely allows transformation of American lager strains with integrating plasmids such as pRD111. The new method, which involves, as have previous methods, the use of antibiotic resistance to select transformants, avoids exposing the yeast cells to heated, molten agar, which we have found kills many or all of the cells. Instead, we expose the cells to the antibiotic by plating the cells on a porous support, e.g., filter paper, which is placed on top of solid, cool medium containing antibiotic, which contacts the cells after diffusing up through the porous support. In more detail, the method is as follows.

Lager strains were isolated from kegs of unpasteurized beer, e.g., Budweiser, by filtration of 500 ml beer through a 0.45 micron Nalgene disposable filter unit. The filter was excised with a sterile scalpel and placed on a petri plate of YEP-D agar (1% Difco Yeast Extract, 2% Difco Bacto-Peptone, 2% dextrose, and 2% agar) containing 20 ug/ml tetracycline and 100 ug/ml ampicillin. Yeast colonies appeared in three days. The yeast strain was identified as a close relative of Saccharomyces cervisiae by DNA hybridization of 2 micron DNA and HO DNA.

For transformation, the lager strains are typically grown to $2 \times 10^7$ cells/ml in YEP-D liquid medium. $4 \times 10^9$ cells are pelleted by centrifugation (all centrifugations are 5,000 rpm for 5 minutes) and rinsed once in 20 ml LTE (0.1M lithium acetate, 0.01M Tris-HCl, pH 7.4, 0.001M $Na_2$ EDTA). The cells are then resuspended in 20 ml LTE and incubated for 30 minutes at 30° C. on a roller drum. Cells are then pelleted, resuspended in 2.0 ml LTE, and aliquoted into 0.2 ml portions. 25 ug of plasmid DNA linearized at a site in the target sequence (for example, the unique SstII site in HO in the case of pRD111) is mixed with 25 ug of sheared calf thymus DNA in a total volume of 25 to 50 ul LTE and added to a 0.2 ml aliquot of treated cells. The mix of DNA and cells is kept on ice for 10 minutes and then is heat shocked in a 38° C. water bath for 5 minutes. After 10 more minutes on ice, 1.0 ml of 40% Polyethyleneglycol 4000 in LTE is mixed with the cell suspension. After 30 minutes on ice, the cells are pelleted and resuspended in 0.2 ml YEP-D. 0.1 ml of this suspension is spread on a Millipore filter (catalog number HATF 082 25) that has been placed flat on the surface of a YEP-D agar 0.1M $KPO_4$, pH 7.0 petri plate. After incubation at 30° for 2 generations (6–8 hours for American lager strains), the filter containing the yeast cells is transferred to a fresh petri plate of YEP-D agar 0.1M $KPO_4$, pH 7.0 plus 200–1000 ug/ml antibiotic G418. Care is taken to avoid bubbles of air between the agar and filters. Transformants appear out the background of untransformed cells as colonies after 3 or 4 days at 30° C. This procedure typically gives about 25–50 transformants per 25 ug of linearized integrating plasmid. The integrated state of the plasmid is routinely confirmed by Southern Blot analysis.

Jettisonning of Vector Sequences

A transformant containing pRD111 integrated at the HO locus is grown for 20–40 generations non-selectively in YEP-D liquid medium and plated at about 500 cells per petri plate on YEP-Gal-XG-BU agar (1% yeast extract, 2% peptone, 2% galactose, 0.006% 5'-bromo-4'-cloro-3'-indoyl-Beta-D-galactoside, 0.1M $KPO_4$, pH 7.0, 2% agar). After 5 days at 30° C., most colonies turn blue. Rare white colonies are picked onto MS agar (0.7% Difco Yeast Nitrogen Base, 2% Fisher soluble starch, 2% agar) to check for growth on starch as a sole carbon source. About one in $10^3$ to $10^4$ colonies are white, and about one in two of the white colonies secrete glucoamylase as evidenced by growth on starch. Confirmation of glucoamylase secretion is routinely checked by Western Blotting and identification of glucoamylase with a rabbit antibody to purified *A. niger* glucoamylase.

Once the gene encoding glucoamylase has been integrated and the unwanted sequences jettisonned, the above-described procedure may be repeated, to integrate additional copies of the gene into other chromosomes, or other locations within a chromosome. This can result, e.g., in the integration of the gene into every chromosome of a host yeast cell having the homologous target region. Creating multiple copies of the gene yields these advantages: 1) increased expression of the gene; 2) increased stability of the resulting strains, perhaps by decreasing the probability of gene conversion which could result in the loss of the gene.

Brewing Strains

A single copy of the TPI-glucoamylase fusion was deposited in one copy of the HO gene of an American lager brewing strain, Brew 1, as described above. The vector sequences were jettisoned and the final structure of the deposited gene was confirmed by Southern Blots. This new strain is called Brew 1/pRD111-R (the R stands for Revertant).

Two batches of beer were simultaneously brewed from the same lot of wort, one batch with Brew 1/pRD111-R and the other with untransformed Brew 1. The wort contained, per liter, 150 grams of Munton and Fison Amber Malt Extract, 0.5 gram Hallertau Hops Pellets, 0.5 gram Burton Water Salts, and 2.0 grams of Yeast Nutrient Salts (Beer and Wine Hobby, Greenwood, Mass. 01880). A 5% innoculum was grown aerobically to saturation in wort and then added to an anaerobic fermentor. After 9 days of fermentation at 15° C., the raw beer was tranferred to a clean fermenter, leaving behind the bulk of the settled yeast, after which the beer was stored for 3 weeks at 15° C.

The fermented beer was then analyzed for the presence of dextrins. A 1 ml sample of beer was treated with 1 ul of a commercial preparation of *A. niger* glucoamylase (DIAZYME 200L$^R$ Miles Laboratories) for 3 hours at 50° C. These conditions had been shown to effect complete digestion of any residual dextrins to glucose. A 25 ul sample of each digest was then analyzed for glucose on a Yellow Springs Instruments Model 27 glucose analyzer. The beer brewed by the transformed strain, Brew 1/pRD111-R, contained substantially reduced levels of dextrin compared to the control beer brewed by untransformed Brew 1. High pressure liquid chromatography of the two beers, using a 10 cm Spheri 5 RC 8 column coupled to a 22 cm Polypore H column (both from Rainin Instruments) and 0.01N $H_2SO_4$ as the eluant, confirmed that residual dextrins were reduced by the engineered strain compared to the control strain.

Deposit

The following deposits have been made with the American Type Culture Collection (ATCC), where the deposits were given the following accession numbers:

| Deposit | Accession No. |
| --- | --- |
| pRY252 | ATCC 39687 |
| pRY253 | ATCC 39688 |
| pRY255 | ATCC 39689 |
| pRY255A | ATCC 39822 |
| pRD111 in *E. coli* YMC9 | ATCC 53123 |

Applicants' assignee, BioTechnica International, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

Other Embodiments

Other embodiments are within the following claims.

For example, although the frequency at which the integrating vectors integrate into the host chromosome is increased by linearizing the vector prior to transformation. integration, at a lower frequency, can be achieved by transformation with the vectors in circularized form. Although the HO gene is the most preferred target gene, any other region of the host chromosome not involved in metabolism can be used. For example, the mutant homothallism gene of most laboratory yeast strains (the ho gene), which differs slightly from the wild-type HO gene, can be used as a target; the ho gene, like the HO gene, has the advantages of large size (about 2,000 base pairs) and non-involvement in metabolism in diploid or polyploid cells.

In addition to enzymes involved in the production of bread and alcoholic beverages, the vectors of the invention can be used in processes in which the desired end product is the protein. e.g., therapeutic proteins such as interferon, encoded by the inserted heterologous gene. The heterologous gene can also be a gene already carried on a different portion of the host chromosome; for example, it might be advantageous to add an additional copy of a native gene involved in alcohol production, to increase production levels.

The promoter sequence controlling the gene for antibiotic resistance can also vary widely, the only crucial factor being that the sequence provides that a sufficient level of expression in yeast cells is maintained.

When a gene in the host chromosome is targeted by employing a vector containing a homologous sequence, linearization of the vector prior to transformation can occur anywhere within the homologous sequence; generally, however, integration efficiency is improved when linearization occurs near the center of the sequence, and decreases as the linearizaton point approaches either end of the sequence.

The screenable trait, in addition to the ability to produce beta-galactosidase, can be any trait whose absence can be detected. In addition, when beta-galactosidase production is used, the gene need not be the E. coli lacZ gene: for example, the LAC4 gene from Kluyeromyces species, e.g., K. lactis, which also encodes a beta-galactosidase, can also be used.

As mentioned above, any suitable aneuploid or diploid or greater ploidy yeast can be used in the invention. Suitable strains include the ones listed below, all of which contain the HO gene, which facilitates integration.

| Strain Name | Species | Type |
| --- | --- | --- |
| Budweiser | S. uvarum | lager |
| ATCC 42928 | S. cerevisiae | wine |
| Fleischman | S. cerevisiae | bread |
| Red Star | S. cerevisiae | bread |
| Red Star Quick Rise | S. cerevisiae | bread |
| 1354 | S. diastaticus | lab |
| DBY 745 | S. cerevisiae | lab |
| DCL-M | S. cerevisiae | distillery |

We claim:

1. An aneuploid, diploid or polyploid industrial Saccharomyces cell transformed with heterologous DNA, or a descendant of said cell, wherein said heterologous DNA is integrated into a chromosome of said Saccharomyces cell.

2. The Saccharomyces cell of claim 1 in which the cell is of a baking yeast strain.

3. The Saccharomyces cell of claim 1 in which the cell is of an ethanol producing yeast strain.

4. The Saccharomyces cell of claim 1, wherein said cell is of a wine producing strain.

5. The Saccharomyces cell of claim 1, wherein said Saccharomyces cell is of the species *Saccharomyces cerevisiae*.

6. The Saccharomyces cell of claim 1, wherein said Saccharomyces cell is of the species *Saccharomyces uvarum*.

7. The Saccharomyces cell of claim 1, wherein said Saccharomyces cell is of the species *Saccharomyces diastaticus*.

8. The Saccharomyces cell of claim 1, wherein said heterologous DNA is integrated into said chromosome such that said DNA is lost from said chromosome at a rate less than $10^{-3}$ over 10–20 generations of non-selective growth.

9. The Saccharomyces cell of claim 1, wherein said heterologous DNA encodes a desired protein.

10. The Saccharomyces cell of claim 9, in which said desired protein is an enzyme.

11. The Saccharomyces cell of claim 10, wherein said enzyme is glucoamylase.

12. The Saccharomyces cell of claim 11 wherein said glucoamylase enables the generation of glucose from starch by said Saccharomyces cell, said glucose being employed as an energy source in a process to produce a product of said Saccharomyces cell.

13. The Saccharomyces cell of claim 12 wherein said product is beer.

14. The Saccharomyces cell of claim 12 wherein said product is a distilled spirit.

15. The Saccharomyces cell of claim 14 wherein said distilled spirit is whiskey.

16. The Saccharomyces cell of claim 1 wherein integration of said heterologous DNA is at a site of said chromosome of a non-expressed gene on said chromosome.

17. The Saccharomyces cell of claim 16 wherein said non-expressed gene is a gene for homothallism.

18. The Saccharomyces cell of any of claims 1, 9, 11, 8, 5, 6, or 7, in which said heterologous DNA is integrated in two or more copies per cell.

19. The Saccharomyces cell of claim 18 in which said two or more copies are located on two or more different chromosomes.

20. The Saccharomyces cell of claim 19 in which said different chromosomes are homologous to each other.

21. The Saccharomyces cell of claim 19 in which said different chromosomes are non-homologous.

22. An aneuploid, diploid or polyploid industrial Saccharomyces cell transformed with a vector, or a descendant of said cell, said vector comprising: (a) a gene which confers resistance to an antibiotic otherwise capable of killing said Saccharomyces cell, said gene which confers resistance being transcribed from a yeast promoter sequence, and (b) heterologous DNA; wherein said heterologous DNA is integrated into a chromosome of said Saccharomyces cell.

23. The Saccharomyces cell of claim 22 in which the cell is of a baking yeast strain.

24. The Saccharomyces cell of claim 22 in which the cell is of an ethanol producing strain.

25. The Saccharomyces cell of claim 22 wherein said gene which confers antibiotic resistance is a gene which confers resistance to G418.

26. The Saccharomyces cell of claim 22 wherein said vector or a portion of said vector is integrated into a chromosome of said Saccharomyces cell such that said integrated DNA is lost from said chromosome at a rate of less than $10^{-3}$ over 10–20 generations of non-selective growth.

27. The Saccharomyces cell of claim 22 wherein said vector further comprises a DNA sequence homologous to at least a portion of a chromosome of said Saccharomyces cell, and said homologous DNA sequence contains none of said promoter sequence.

28. The Saccharomyces cell of claim 27 wherein said portion of said chromosome comprises at least a portion of the gene for homothallism (HO) of said Saccharomyces cell.

29. The Sacchromyces cell of claim 22, wherein said heterologous DNA encodes a desired protein and is transcribed from a promoter sequence different from the promoter sequence from which said gene for antibiotic resistance is transcribed.

30. The Sacchromyces cell of claim 29 wherein said promoter sequence of said heterologous DNA is more highly expressed than said promoter sequence of said antibiotic resistance gene.

31. The Sacchromyces cell of claim 29 wherein said heterologous DNA encodes an enzyme.

32. The Sacchromyces cell of claim 31 wherein said enzyme comprises glucoamylase.

33. The Saccharomyces cell of claim 32 wherein said glucoamylase enables the generation of glucose from starch by said Saccharomyces cell, said glucose being employed as an energy source in a process to produce a product of said Saccharomyces cell.

34. The Saccharomyces cell of claim 33 wherein said product is beer or ale.

35. The Saccharomyces cell of claim 33 wherein said product is a distilled spirit.

36. The Saccharomyces cell of claim 35 wherein said distilled spirit is whiskey.

37. The Saccharomyces cell of claim 27 wherein:
(a) said vector is linearized;
(b) the chromosomal DNA of said Saccharomyces cell comprises a target, said target comprising, in the following order,
 (i) a first end of said target,
 (ii) a first target sequence bounded by said first end and by a site $L_c$,
 (iii) said site $L_c$,
 (iv) a second target sequence bounded by said site $L_c$ and by a site $S_c$,
 (v) said site $S_c$,
 (vi) a third target sequence bounded by said site $S_c$ and by a second end of said target, and
 (vii) said second end of said target;
(c) said vector comprises
 (i) a first sequence homologous with said second target sequence,
 (ii) a second sequence homologous with said first target sequence,
 (iii) a third sequence homologous with said third target sequence,
 (iv) said heterologous DNA,
 (v) said gene conferring said antibiotic resistance; and
(d) said first sequence and said second sequence are separated from each other on said linearized vector by a region of partial non-homology which comprises:
 (i) said heterologous DNA,
 (ii) said third sequence homologous with said third target sequence,
 (iii) said gene conferring said antibiotic resistance.

38. The Saccharomyces cell of claim 37 wherein said heterologous DNA encodes glucoamylase.

39. The Saccharomyces cell of claim 37 wherein said vector further comprises a gene for a screenable trait and said sequences are arranged on said linearized vector in the order
said first homologous sequence,
said heterologous DNA,
said third homologous sequence,
said gene for a screenable trait,
said antibiotic resistance gene, and
said second homologous sequence.

40. The Sacchromyces cell of claim 39 wherein said gene for a screenable trait comprises a gene encoding beta-galactosidase.

41. An aneuploid, diploid or greater ploidy industrial Saccharomyces cell transformed with DNA encoding glucoamylase, or a descendant of said cell, wherein said Saccharomyces cell is capable of expressing enzymatically active glucoamylase from said DNA, and said DNA is integrated into a chromosome of said Saccharomyces cell.

42. The Saccharomyces cell of claim 41 wherein said glucoamylase-encoding DNA, prior to transformation, is carried on a cloning vector.

43. The Saccharomyces cell of claims 41 or 1, wherein said transformation of said cell does not substantially impair the flavor of a product produced by said cell.

44. The Saccharomyces cell of claim 43 wherein said product is beer or ale.

45. The Saccharomyces cell of claim 43 wherein said product is a distilled spirit.

46. The Saccharomyces cell of claim 45 wherein said distilled spirit is whiskey.

47. An aneuploid or diploid or greater ploidy industrial Saccharomyces cell transformed with a vector, or a descendant of said transformed cell, said vector containing expressible DNA encoding glucoamylase, DNA encoding a selectable trait, and a DNA sequence homologous with a chromosomal sequence of said Saccharomyces cell; wherein said DNA encoding glucoamylase is integrated into a chromosome of said Saccharomyces cell.

48. The Saccharomyces cell of claim 47 in which the cell is of a baking yeast strain.

49. The Saccharomyces cell of claim 47 in which the cell is of an ethanol producing strain.

50. The Saccharomyces cell of claim 47 wherein said glucoamylase enables the generation of glucose from starch by said Saccharomyces cell, said glucose being employed as an energy source in a process to produce a product of said Saccharomyces cell.

51. The Saccharomyces cell of claim 50 wherein said product is beer or ale.

52. The Saccharomyces cell of claim 50 wherein said product is a distilled spirit.

53. The Saccharomyces cell of claim 52 wherein said distilled spirit is whiskey.

54. The Saccharomyces cell of claim 47 wherein:
(a) said vector is linearized;
(b) said chromosomal sequence of said Saccharomyces cell comprises a target, said target comprising, in the following order,
(i) a first end of said target,
(ii) a first target sequence bounded by said first end and by a site $L_c$,
(iii) said site $L_c$,
(iv) a second target sequence bounded by said site $L_c$ and by a site $S_c$,
(v) said site $S_c$,
(vi) a third target sequence bounded by said site $S_c$ and by a second end of said target, and
(vii) said second end of said target;
(c) said vector comprises
(i) a first sequence homologous with said second target sequence,
(ii) a second sequence homologous with said first target sequence,
(iii) a third sequence homologous with said third target sequence,
(iv) said DNA encoding glucoamylase,
(v) said DNA encoding a selectable trait, and
(vi) DNA encoding a screenable trait; and
(d) said first sequence and said second sequence are separated from each other on said linearized vector by a region of partial non-homology which comprises
(i) said DNA encoding glucoamylase,
(ii) said third sequence homologous with said third target sequence,
(iii) said DNA encoding a selectable trait, and
(iv) said DNA encoding a screenable trait.

55. The Sacchromyces cell of claim 54 wherein said DNA encoding a selectable trait is a gene for antibiotic resistance and said DNA encoding a screenable trait is a *lacZ* gene.

56. The Sacchromyces cell of claim 54 wherein said sequences are arranged on said linearized vector in the order
said first homologous sequence,
said DNA encoding glucoamylase,
said third homologous sequence,
said DNA encoding a screenable trait,
said DNA encoding a selectable trait, and
said second homologous sequence.

* * * * *